US011832920B2

(12) United States Patent
White et al.

(10) Patent No.: US 11,832,920 B2
(45) **Date of Patent: *Dec. 5, 2023**

(54) DEVICES, SYSTEMS, AND METHODS FOR PULMONARY ARTERIAL HYPERTENSION (PAH) ASSESSMENT AND TREATMENT

(71) Applicant: ST. JUDE MEDICAL LUXEMBOURG HOLDINGS II S.A.R.L. ("SJM LUX II"), Luxembourg (LU)

(72) Inventors: Jason White, Smyrna, GA (US); Ralph Jordan, Atlanta, GA (US); John Erik Moore, Roswell, GA (US); Jay Yadav, Sandy Springs, GA (US)

(73) Assignee: ST. JUDE MEDICAL LUXEMBOURG HOLDINGS II S.A.R.L. ("SJM LUX II"), Luxembourg (LU)

( * ) Notice: Subject to any disclaimer, the term of this patent is extended or adjusted under 35 U.S.C. 154(b) by 643 days.

This patent is subject to a terminal disclaimer.

(21) Appl. No.: 16/893,542

(22) Filed: Jun. 5, 2020

(65) Prior Publication Data

US 2020/0297218 A1 Sep. 24, 2020

Related U.S. Application Data

(63) Continuation of application No. 14/086,478, filed on Nov. 21, 2013, now Pat. No. 10,709,341.
(Continued)

(51) Int. Cl.
*A61B 5/0215* (2006.01)
*G16H 50/20* (2018.01)

(Continued)

(52) U.S. Cl.
CPC ............ *A61B 5/0215* (2013.01); *A61B 5/002* (2013.01); *A61B 5/029* (2013.01);
(Continued)

(58) Field of Classification Search
CPC ....... A61B 5/02; A61B 5/0215; A61B 5/7275; A61B 2562/0247
See application file for complete search history.

(56) References Cited

U.S. PATENT DOCUMENTS 5,368,040 A 11/1994 Carney
5,817,320 A 10/1998 Stone (Continued)

FOREIGN PATENT DOCUMENTS

WO 2006023603 A3 3/2006
WO 2013142387 A1 9/2013

(Continued)

OTHER PUBLICATIONS

Mundt et al., "Glycoprotein J of infectious laryngotracheitis virus is required for efficient egress of infectious virions from cells", Journal of General Virology (2011), 92, 2586-2589 (4 pages).
(Continued)

*Primary Examiner* — Puya Agahi
(74) *Attorney, Agent, or Firm* — The Small Patent Law Group, LLC; Dean D. Small

(57) ABSTRACT

Provided herein are devices, systems, and methods for assessing, treating, and for developing new treatments for pulmonary arterial hypertension (PAH) using pulmonary artery pressure (PAP) values and/or cardiac output (CO) estimates.

20 Claims, 7 Drawing Sheets

Related U.S. Application Data

(60) Provisional application No. 61/799,536, filed on Mar. 15, 2013, provisional application No. 61/728,913, filed on Nov. 21, 2012.

(51) Int. Cl.
    *A61B 5/029*     (2006.01)
    *A61B 5/02*     (2006.01)
    *A61B 5/00*     (2006.01)
    *G16H 20/10*     (2018.01)

(52) U.S. Cl.
    CPC .......... *A61B 5/02028* (2013.01); *A61B 5/686* (2013.01); *A61B 5/7275* (2013.01); *A61B 5/7282* (2013.01); *G16H 20/10* (2018.01); *G16H 50/20* (2018.01); *A61B 5/02* (2013.01); *A61B 2560/0219* (2013.01); *A61B 2560/0228* (2013.01); *A61B 2562/0247* (2013.01)

(56) References Cited

U.S. PATENT DOCUMENTS

| | | |
|---|---|---|
| 6,033,670 A | 3/2000 | Bublot et al. |
| 6,153,199 A | 11/2000 | Audonnet et al. |
| 6,277,078 B1 | 8/2001 | Porat et al. |
| 6,705,990 B1 | 3/2004 | Gallant et al. |
| 6,970,742 B2 | 11/2005 | Mann et al. |
| 7,024,244 B2 | 4/2006 | Muhlenberg et al. |
| 7,367,951 B2 | 5/2008 | Bennett et al. |
| 7,481,771 B2 | 1/2009 | Fonseca et al. |
| 7,569,572 B2 | 8/2009 | Bell et al. |
| 7,594,889 B2 | 9/2009 | St. Ores et al. |
| 7,615,010 B1 | 11/2009 | Najafi et al. |
| 7,646,901 B2 | 1/2010 | Murphy et al. |
| 7,654,964 B1 | 2/2010 | Kroll et al. |
| 7,679,355 B2 | 3/2010 | Allen et al. |
| 7,699,059 B2 | 4/2010 | Fonseca et al. |
| 7,949,394 B2 | 5/2011 | Salo et al. |
| 8,026,729 B2 | 9/2011 | Kroh et al. |
| 8,127,618 B1 | 3/2012 | Zhao et al. |
| 8,147,415 B2 | 4/2012 | Liao et al. |
| 8,147,416 B2 | 4/2012 | Fayram et al. |
| 8,231,539 B2 | 7/2012 | Bardy |
| 8,273,031 B2 | 9/2012 | Cohen et al. |
| 8,278,941 B2 | 10/2012 | Kroh et al. |
| 8,301,252 B2 | 10/2012 | Hatlestad et al. |
| 8,303,511 B2 | 11/2012 | Eigler et al. |
| 8,545,436 B2 | 10/2013 | Robertson et al. |
| 8,665,086 B2 | 3/2014 | Miller et al. |
| 9,198,908 B2 | 12/2015 | Yadav |
| 2001/0016690 A1 | 8/2001 | Chio |
| 2002/0032384 A1 | 3/2002 | Raymond et al. |
| 2003/0036683 A1 | 2/2003 | Kehr et al. |
| 2003/0199779 A1 | 10/2003 | Muhlenberg et al. |
| 2004/0147981 A1 | 7/2004 | Bardy |
| 2005/0015014 A1 | 1/2005 | Fonseca et al. |
| 2006/0047205 A1 | 3/2006 | Ludomirsky et al. |
| 2006/0281681 A1 | 12/2006 | Pilon |
| 2007/0043591 A1 | 2/2007 | Meretei et al. |
| 2007/0088221 A1 | 4/2007 | Stahmann |
| 2007/0250121 A1 | 10/2007 | Miesel et al. |
| 2007/0282210 A1 | 12/2007 | Stern |
| 2008/0077375 A1 | 3/2008 | Fernandez |
| 2008/0077440 A1 | 3/2008 | Doron |
| 2008/0243007 A1 | 10/2008 | Liao et al. |
| 2008/0243016 A1 | 10/2008 | Liao et al. |
| 2008/0300650 A1 | 12/2008 | Gerber et al. |
| 2009/0006061 A1 | 1/2009 | Thukral et al. |
| 2009/0030291 A1 | 1/2009 | O'Brien et al. |
| 2009/0054793 A1 | 2/2009 | Nunez et al. |
| 2009/0062313 A1 | 3/2009 | Kass et al. |
| 2009/0177106 A1 | 7/2009 | Ricke et al. |
| 2009/0197922 A1 | 8/2009 | Maitland et al. |
| 2009/0239883 A1 | 9/2009 | Butrous et al. |
| 2009/0320836 A1 | 12/2009 | Baker, Jr. |
| 2010/0056931 A1 | 3/2010 | Soffer et al. |
| 2010/0094144 A1 | 4/2010 | Doron |
| 2010/0274221 A1 | 10/2010 | Sigg et al. |
| 2010/0286535 A1 | 11/2010 | Blomqvist |
| 2010/0305414 A1 | 12/2010 | Koo et al. |
| 2011/0003610 A1 | 1/2011 | Key et al. |
| 2011/0098767 A1 | 4/2011 | Sugimachi et al. |
| 2011/0106200 A1 | 5/2011 | Ziegler |
| 2011/0125023 A1 | 5/2011 | Palti et al. |
| 2011/0144150 A1 | 6/2011 | Lampe et al. |
| 2011/0144967 A1 | 6/2011 | Adirovich |
| 2011/0201949 A1 | 8/2011 | Bodecker et al. |
| 2011/0273287 A1 | 11/2011 | LaLOnde et al. |
| 2012/0004188 A1 | 1/2012 | Belardinelli |
| 2012/0064006 A1 | 3/2012 | Yadav |
| 2012/0065165 A1 | 3/2012 | Aspland et al. |
| 2012/0071735 A1 | 3/2012 | Caylor, III et al. |
| 2012/0100155 A1 | 4/2012 | Stoloff et al. |
| 2012/0136583 A1 | 5/2012 | Azar et al. |
| 2013/0044704 A1 | 2/2013 | Pang et al. |
| 2013/0224306 A1 | 8/2013 | Gillies et al. |
| 2013/0245469 A1 | 9/2013 | Yadav et al. |
| 2014/0275861 A1 | 9/2014 | Kroh et al. |
| 2014/0288085 A1 | 9/2014 | Yadav |
| 2015/0133796 A1 | 5/2015 | Yadav |

FOREIGN PATENT DOCUMENTS

| | | |
|---|---|---|
| WO | 2014145531 A3 | 9/2014 |
| WO | 2014145712 A1 | 9/2014 |
| WO | 2012019191 A3 | 2/2019 |

OTHER PUBLICATIONS

Weitzenblum, "Chronic Cor Pulmonale", Heart (2003), 89:225-230 (6 pages).

Spatz et al., "Comparative full genome analysis of four infectious laryngotracheitis virus (Gallid herpesvirus-1) virulent isolates from the United States", Virus Genes (2012) 44:273-285 (13 pages).

Non-Final Office Action for U.S. Appl. No. 14/216,582 dated Dec. 5, 2014 (11 pages).

Non-Final Office Action for U.S. Appl. No. 14/216,582 dated Mar. 16, 2015 (21 pages).

Non-Final Office Action for U.S. Appl. No. 13/843,553 dated Jul. 2, 2015 (37 pages).

Non-Final Office Action for U.S. Appl. No. 13/205,459 dated Aug. 6, 2014 (24 pages).

Non-Final Office Action for U.S. Appl. No. 13/205,459 dated Aug. 6, 2013 (22 pages).

Final Office Action for U.S. Appl. No. 13/205,459 dated May 1, 2014 (26 pages).

Naeije, "Pulmonary Hypertension and Right Heart Failure in Chronic Obstructive Pulmonary Disease", Proc Am Thorac Soc vol. 2. pp. 20-22, 2005 (3 pages).

Johnson et al., "Protection Against Infectious Laryngotracheitis by In Ovo Vaccination with Commercially Available Viral Vector Recombinant Vaccines", Avian Diseases, 54(4):1251-1259, 2010 (10 pages).

Guazzi et al., "Pulmonary Hypertension Due to Left Heart Disease", Circulation, 2012, 126:975-990 (16 pages).

Grignola, "Hemodynamic assessment of pulmonary hypertension", World Journal of Cardiology, 2011, 3(1): 10-17 (8 pages).

Fuchs, "In Vitro and In Vivo Relevance of Infectious Laryngotracheitis Virus gJ Proteins That Are Expressed from Spliced and Nonspliced mRNAs", Journal of Virology, 2005, vol. 79, No. 2, p. 705-716 (12 pages).

Fruhwald et al., "Continuous Hemodynamic Monitoring in Pulmonary Hypertensive Patients Treated With Inhaled Iloprost", Chest, 2003, 124;351-359 (11 pages).

Frantz, "Hemodynamic monitoring in pulmonary arterial hypertension", Expert Rev. Resp. Med. 5(2), 173-178 (2011) (6 pages).

Frantz et al., "Continuous Hemodynamic Monitoring in Patients With Pulmonary Arterial Hypertension", The Journal of Heart and Lung Transplantation, 2008, vol. 27, No. 7, 780-788 (9 pages).

(56) References Cited

OTHER PUBLICATIONS

International Preliminary Report on Patentability for International Application No. PCT/US2011/046953 dated Feb. 12, 2013 (7 pages).
International Preliminary Report on Patentability for International Application No. PCT/US2013/032642 dated Sep. 23, 2014 (10 pages).
International Preliminary Report on Patentability for International Application No. PCT/US2013/071294 dated May 26, 2015 (8 pages).
International Preliminary Report on Patentability for International Application No. PCT/US2014/030322 dated Sep. 15, 2015 (8 pages).
International Preliminary Report on Patentability for International Application No. PCT/US2014/030521 dated Sep. 15, 2015 (11 pages).
International Search Report for International Application No. PCT/US2011/046953 dated Feb. 29, 2012 (3 pages).
International Search Report for International Application No. PCT/US2013/32642 dated Jul. 19, 2013 (4 pages).
International Search Report for International Application No. PCT/US2013/071294 dated Feb. 7, 2014 (4 pages).
International Search Report for International Application No. PCT/US2014/030521 dated Aug. 8, 2014 (4 pages).
International Search Report for International Application No. PCT/US2014/30322 dated Apr. 13, 2015 (11 pages).

DEVICES, SYSTEMS, AND METHODS FOR PULMONARY ARTERIAL HYPERTENSION (PAH) ASSESSMENT AND TREATMENT

CROSS-REFERENCE TO RELATED APPLICATIONS

The present application is a continuation application of, and claims priority to U.S. application Ser. No. 14/086,478, filed Nov. 21, 2013 which claims benefit of U.S. Provisional Application No. 61/728,913, filed Nov. 21, 2012, and U.S. Provisional Application No. 61/799,536, filed Mar. 15, 2013, each of which are hereby incorporated herein by reference in their entirety.

TECHNICAL FIELD

This application generally relates to devices, systems, and methods for the assessment and treatment of pulmonary arterial hypertension (PAH).

BACKGROUND

Pulmonary arterial hypertension (PAH) is a progressive disease that results in elevation of the pulmonary artery pressure and ultimately development of right ventricular failure. Baseline and periodic invasive hemodynamics via right heart catheterization are generally obtained in order to characterize and follow the extent of hemodynamic derangement, response to therapy, and as an end point in clinical trials of novel therapy.

SUMMARY

Provided herein are methods for assessing, treating, and for developing new treatments for PAH.

For example, provided are methods for evaluating progress of pulmonary arterial hypertension (PAH) in a subject, or an outcome in a subject having PAH. Example methods include obtaining a pulmonary artery pressure waveform from the subject. One or more pulmonary artery pressure (PAP) values are determined from the pulmonary artery waveform. Cardiac output (CO) is estimated using the pulmonary artery pressure waveform. One or more of the PAP values and one or more of the CO estimates are compared to standard PAP and CO values respectively. The comparisons of PAP and CO are used to monitor the PAH progression or outcome in the subject.

An agent can be administered to the subject, and determined PAP values and estimated CO values, in combination, can be used for evaluating treatment of a subject having PAH. In this regard, an example method includes administering an agent to the subject and obtaining a pulmonary artery pressure waveform from the subject. One or more pulmonary artery pressure (PAP) values are determined from the pulmonary artery waveform. Cardiac output (CO) is estimated using the pulmonary artery pressure waveform. One or more of the PAP values and one or more of the CO estimates are compared to standard PAP and CO values respectively, for example, to determine trends in PAP values and CO estimates in the subject. The comparisons of PAP and CO, for example trends, are used to monitor the effect of the administered agent on the PAH condition in the subject.

Additional methods for evaluating treatment of a subject having PAH include administering an agent to the subject and obtaining a pulmonary artery pressure waveform from the subject. One or more pulmonary artery pressure (PAP) values are determined from the pulmonary artery waveform and are compared to a standard PAP value. The comparison of PAP is used to monitor the effect of the administered agent on the PAH condition in the subject. A decrease in the one or more determined PAP values compared to the PAP standard, for example a decreasing trend in the subject's PAP values, indicates a beneficial effect of the administered agent on the PAH condition in the subject. An increase in the one or more determined PAP values compared to the PAP standard, for example an increasing trend in the subject's PAP values, indicates no beneficial effect of the administered agent on the PAH condition in the subject.

Additional methods for evaluating treatment of a subject having PAH include administering an agent to the subject and obtaining a pulmonary artery pressure waveform from the subject. Cardiac output (CO) is estimated using the pulmonary artery pressure waveform and compared to a standard CO value. The comparison of CO is used to monitor the effect of the administered agent on the PAH condition in the subject. In this method, an increase in the one or more estimated CO values compared to the CO standard, for example an increasing trend in the subject's CO estimates, indicates a beneficial effect of the administered agent on the PAH condition in the subject. A decrease in the one or more estimated CO values compared to the CO standard, for example a decreasing trend in the subject's CO estimated values, indicates no beneficial effect of the administered agent on the PAH condition in the subject.

Optionally, the standard PAP value in the methods described herein is one or more previously determined PAP values from the subject. For example, the standard is optionally a PAP value determined by obtaining a pulmonary artery pressure waveform from the subject and using that waveform to determine the PAP value. In this way, trends in PAP values in the subject can be monitored. These trends are optionally used to monitor PAH progression or outcome in the subject.

For example, a lowering trend in PAP values over time in, optionally, a subject having PAH, indicates improvement in the PAH condition. This can also optionally indicate improved outcome in the subject, such as, for example, reduced hospitalizations, lower mortality, or lower morbidity.

The trends of PAP are optionally combined with the determination and monitoring of trends in CO in the subject to evaluate the progress of PAH in the subject. For example, the standard CO value, which can be used to determine such trends, is optionally based on one or more previously estimated CO values from the subject, or established normal ranges. A rising trend in CO estimates over time in, optionally, a subject having PAH, indicates improvement in the PAH condition. This can also optionally indicate or predict improved outcome in the subject, such as, for example, reduced hospitalizations, lower mortality, lower morbidity, or improved exercise tolerance. The standard PAP or CO value can also optionally be established normal hemodynamic values, such as PAP and/or CO values. Normal hemodynamic values include normal values for a given subject or population.

The details of one or more embodiments are set forth in the accompanying drawings and the description below. Other features, objects, and advantages will be apparent from the description and drawings, and from the claims.

DETAILED DESCRIPTION

Figure 1:
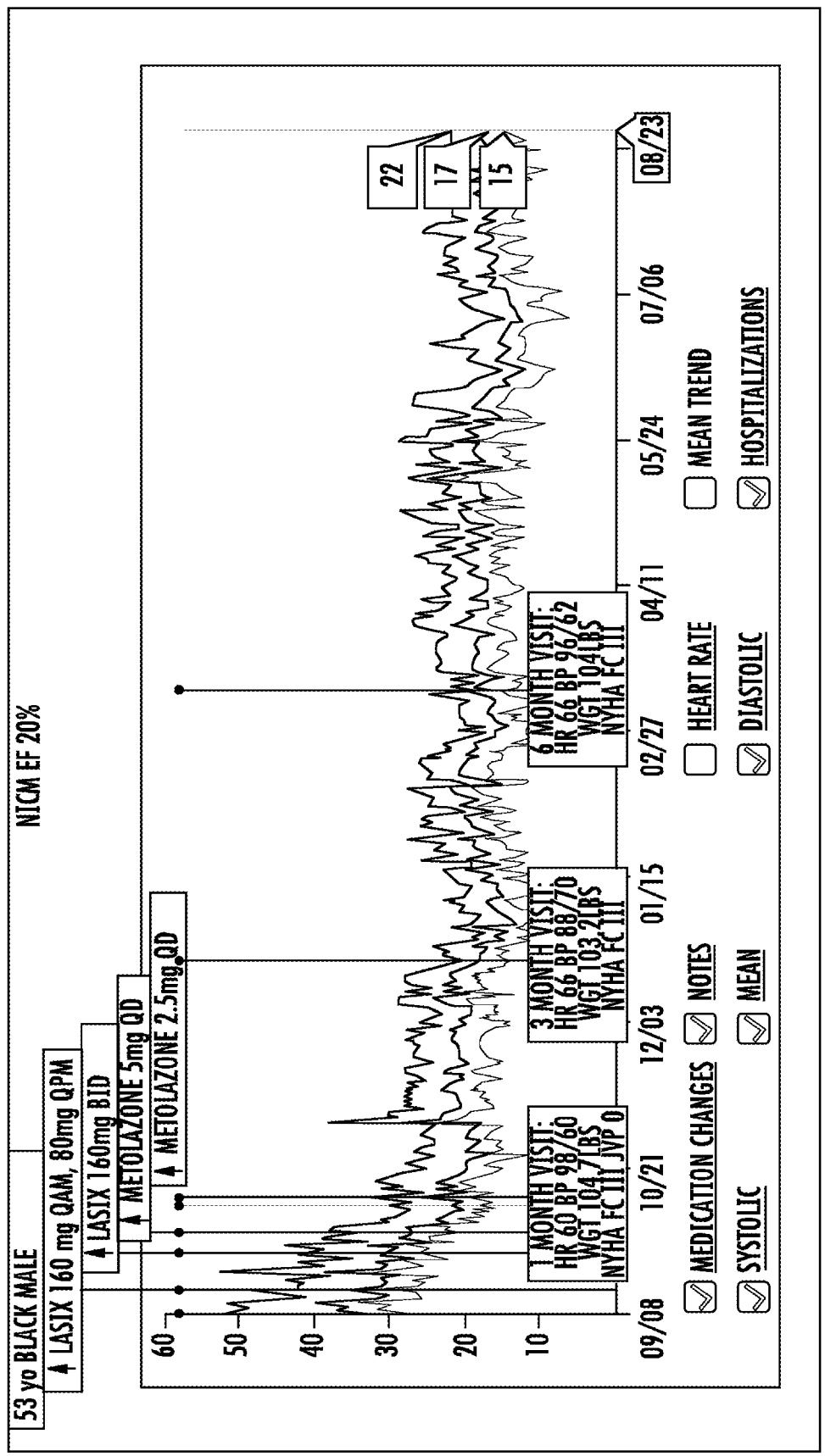
FIG. 1 is a graph showing monitoring of PAP in a subject with PAH prior to and subsequent to administration of therapy to the subject.

Progressive right ventricular failure is a common consequence of PAH and is the leading cause of premature death. In the original NIH pulmonary hypertension registry, a prognostic equation was developed that included right atrial pressure, pulmonary artery pressure, and cardiac index. Right atrial pressure, cardiac index, and PAP were significant factors with respect to outcome, listed in order of statistical importance. While RA pressure has a high correlation with outcomes, this is because it is a direct symptom of RV failure, which occurs in the latter stage of the disease progression when treatment options are limited, and RV failure has a high correlation with outcomes. However, the diagnostic usefulness of this parameter in the earlier stages of the disease progression is limited.

CO and PAP provide an indication of the ventricular stroke work, which when elevated over extended timeframes, overloads the RV and accelerate RV failure. Calculated parameters such as Stroke Work (mPAP×Stroke Volume) and Total Pulmonary Resistance (TPR) (mPAP/CO) use PAP and CO together to provide an assessment of the RV workload. Pulmonary artery pressure and pulmonary arterial pressure are used synonymously throughout.

Example inventions described herein are based on the use of PAP, CO, and other relevant metrics calculated from these parameters such as Stroke Work and TPR, alone or in combination, can be used to assess, treat, and develop new treatments for PAH and heart failure resulting from PAH. The provided methods are optionally used for evaluating progress of pulmonary arterial hypertension (PAH) in a subject, or an outcome in a subject having PAH.

The methods described herein are optionally used to develop a therapeutic agent. The term "developing" or "development" as used herein in reference to therapeutics are broad terms that include, by way of example and not limitation, prospective design, or selection, of one or more potential therapeutic methods or compounds or retrospective study of one or more therapeutic methods or compounds or design of studies of such therapeutic methods or compounds. In this regard, to develop or development of a therapeutic can include, for example, changes to an active ingredient or formulation and also includes, for example, study design for a therapeutic. Optionally, study design is for a clinical trial and development of a study design can include establishing trial metrics or trial durations.

The methods described herein can also be used to identify a candidate therapeutic agent for administration to a patient. All or a subset of the hemodynamic data, such as, for example, CO estimates and/or PAP values, can be correlated with the candidate therapeutic agent to indicate a predicted change in one or more hemodynamic values in the patient that would result from administration of the candidate agent. The predicted change can be used to indicate the predicted effect of the candidate agent on the hemodynamic parameter of the subject.

A change in one or more of the measured hemodynamic values, such as, for example, CO estimates and/or PAP values resulting from the administration of the therapeutic agent can be identified, the change indicating an effect of the therapeutic agent on the hemodynamic parameter of the subject. Optionally, the hemodynamic data comprises at least one hemodynamic value measured in a subject prior to administration of the therapeutic agent. Optionally, the hemodynamic data comprises at least one hemodynamic value measured in a subject concurrent with administration of the therapeutic agent. Optionally, the hemodynamic data comprises at least one hemodynamic value measured in a subject subsequent to administration of the therapeutic agent. Optionally, the hemodynamic data comprises at least one hemodynamic value measured in a subject prior to administration of the therapeutic agent and at least one hemodynamic value measured in a subject subsequent to administration of the therapeutic agent. In some aspects, one or more additional therapeutic agents are administered to the subject prior to, concurrently with, or subsequent to the therapeutic agent.

Optionally, the therapeutic agent can be modified to increase the indicated effect. For example, if the indicated effect is desired, the structure of the therapeutic agent can be modified to increase the indicated effect. The therapeutic agent can also be modified to decrease the indicated effect. For example, if the indicated effect is not desirable, then the structure of the therapeutic agent can be modified to decrease the indicated effect. Moreover, an administration characteristic of the therapeutic agent can be modified to increase or decrease the indicated effect.

The administration characteristic can be selected from the group consisting of dosage amount, number of doses, timing of doses, route of administration, and total dosage. When the indicated effect is to be increased or decreased, one or more portions of the therapeutic agent responsible for the indicated effect can be determined. Optionally, a second therapeutic agent including the one or more portions of the therapeutic agent responsible for the indicated effect can be designed.

The indicated effect can used to assess safety of the therapeutic agent for administration to a mammal or population thereof. In some examples, the indicated effect is used to assess the toxicity of the therapeutic agent for administration to a mammal or population thereof. Optionally, the toxicity is cardiac toxicity. The indicated effect can also be used to assess the efficacy of the therapeutic agent for administration to a mammal or population thereof. And, the indicated effect can also be used to predict the effect or effects of the therapeutic agent or agents having the same or similar pharmacological characteristics on the hemodynamic parameter. Optionally, the indicated effect is used to predict the effect or effects of the therapeutic agent or agents having the same or similar pharmacological characteristics on a hemodynamic parameter of a mammal. In some aspects, the indicated effect is used to determine an end point for a clinical trial.

The described methods can further comprise determining one or more characteristics of the subject. The determined characteristic can be a physical, physiologic, metabolic, chronological, disease state, drug administration history, medical history, or genetic characteristic.

The characteristic can be correlated with the indicated effect in the subject. The correlation of the characteristic and the indicated effect in the subject can be used to select one or more additional subjects for administration of the therapeutic agent or for a therapeutic agent having the same or similar indicated effect. The correlation of the characteristic and the indicated effect can also be used to select one or more additional subjects to participate in a clinical trial for the therapeutic agent or for a therapeutic agent having the same or similar indicated effect.

These determinations can be used to facilitate development of a therapeutic by efficiently identifying preferred dosages that are correlated to improved physiological data for clinical trials. The determinations can also be used for determining proper dosages of commercial products for general and specific populations of subjects. For example, the described methods can be used to arrive at dosing levels based on patient/subject profiles including, but not limited to, pulmonary artery pressure response and/or cardiac output response to a study or commercial drug or with other hemodynamic metrics alone or in combination with characteristics such as age, weight and concurrent drug administration or drug-drug interaction. Example methods for facilitating development of therapeutics include methods for evaluating progress or outcome in PAH subjects, and for evaluating treatment in PAH subjects. These methods can also be used in clinical treatment and management of subjects.

Example methods include obtaining a pulmonary artery pressure waveform from the subject. One or more pulmonary artery pressure (PAP) values are determined from the pulmonary artery waveform. Cardiac output (CO) is estimated using the pulmonary artery pressure waveform. One or more of the PAP values and one or more of the CO estimates are compared to standard PAP and CO values respectively. The comparisons of PAP and CO are used to monitor the PAH progression or outcome in the subject.

Optionally, the standard PAP value is one or more previously determined PAP values from the subject. For example, the standard is optionally a PAP value determined by obtaining a pulmonary artery pressure waveform from the subject and using that wave form to determine the PAP value. In this way, trends in PAP values in the subject can be monitored. These trends are optionally used to monitor PAH progression or outcome in the subject.

For example, a lowering trend in PAP values over time in, optionally, a subject having PAH indicates improvement in the PAH condition. This can also optionally indicate improved outcome in the subject, such as, for example, reduced hospitalizations, lower mortality, or lower morbidity.

The trends of PAP are optionally combined with the determination and monitoring of trends in CO in the subject to evaluate the progress of PAH in the subject. For example, the standard CO value, which can be used to determine such trends, is optionally based on one or more previously estimated CO values from the subject.

The standard PAP value can also optionally be a clinically relevant target PAP value for the subject and the standard CO value can optionally be a clinically relevant CO target value for the subject. For example, an optional clinical target standard is a PAP of about 25 mmHg. Optionally, the determined PAP value is less than 25 mmHg. The clinically relevant target for either CO or PAP can be, for example, determined by a health care professional treating or managing the PAH subject. A clinically relevant target value can be a value that is a normal value for the subject, or a population of which the subject is a member, or an improved value for the subject, goal value for the subject, or any other value determined by a health care professional managing the subject.

Optionally, one or more PAP values of the subject determined prior to determining the PAP value from the obtained pulmonary artery pressure waveform are greater than 25 mmHg. The clinically relevant target for either CO or PAP can be, for example, determined by a health care professional treating or managing the PAH subject.

Thus, trends in PAP and CO can be monitored relative to previous values from the subject or to clinical target values that may optionally be determined by a health care professional treating or managing the subject.

The trends can be used to determine if the subject is improving. For example, a decrease in the one or more PAP values compared to the standard PAP value, combined with one or more increased or stable CO estimates compared to the standard CO value can indicate or predict improvement in the subject. In another example, one or more stable PAP values compared to the standard PAP value, combined with one or more increased CO estimates compared to the CO standard value indicates or predicts improvement of the PAH in the subject.

Alternatively, a decrease in one or more CO estimates compared to the standard CO value, combined with one or more increased or stable PAP values compared to the standard PAP value can indicate or predict worsening of the PAH in the subject. In another example, an increase in one or more PAP values compared to the standard PAP values, combined with a stable or decreased CO value compared to the standard CO value indicates or predicts worsening of the PAH in the subject. Optionally, as described above, trends in PAP values and trends in CO value are used together to monitor progress or to predict outcome in subjects having PAH.

In other examples, however, PAP value trends or CO value trends are used independently to monitor progress or to predict outcomes in subjects having PAH.

For example, a method for evaluating treatment of a subject having PAH includes administering an agent to the subject and obtaining a pulmonary artery pressure waveform from the subject. One or more pulmonary artery pressure (PAP) values are determined from the pulmonary artery waveform and are compared to a standard PAP value. The comparison of PAP is used to monitor the effect of the administered agent on the PAH condition in the subject. In this way, trends in PAP values independent of CO values are used to evaluate treatment of the subject for the PAH condition. A decrease in the one or more determined PAP values compared to the PAP standard, for example a decreasing trend in the subject's PAP values, indicates a beneficial effect of the administered agent on the PAH condition in the subject. An increase in the one or more determined PAP values compared to the PAP standard, for example an increasing trend in the subject's PAP values, indicates no beneficial effect of the administered agent on the PAH condition in the subject.

In regard to CO, independent of PAP, an example method for evaluating treatment of a subject having PAH includes administering an agent to the subject and obtaining a pulmonary artery pressure waveform from the subject. Cardiac output (CO) is estimated using the pulmonary artery pressure waveform and compared to a standard CO value. The comparison of CO is used to monitor the effect of the administered agent on the PAH condition in the subject. In this way, trends in estimated CO values, independent of PAP values, are used to evaluate treatment of the subject for the PAH condition. In this method, an increase in the one or more estimated CO values compared to the CO standard, for example an increasing trend in the subject's CO estimates, indicates a beneficial effect of the administered agent on the PAH condition in the subject. A decrease in the one or more estimated CO values compared to the CO standard, for example a decreasing trend in the subject's CO estimated values, indicates no beneficial effect of the administered agent on the PAH condition in the subject.

In regard to use of determined PAP values and estimated CO values, in combination, for evaluating treatment of a subject having PAH, an example method includes administering an agent to the subject and obtaining a pulmonary artery pressure waveform from the subject. One or more pulmonary artery pressure (PAP) values are determined from the pulmonary artery waveform. Cardiac output (CO) is estimated using the pulmonary artery pressure waveform. One or more of the PAP values and one or more of the CO estimates are compared to standard PAP and CO values respectively, for example to determine trends in PAP values and CO estimates in the subject. The comparisons of PAP and CO, for example trends, are used to monitor the effect of the administered agent on the PAH condition in the subject.

The trends can be used to determine the effect of the administered agent on the PAH condition in the subject. For example, a decrease in the one or more PAP values compared to the standard PAP value, combined with one or more increased or stable CO estimates compared to the standard CO value can indicates a beneficial effect of the administered agent on the PAH condition in the subject. In another example, one or more stable PAP values compared to the standard PAP value, combined with one or more increased CO estimates compared to the CO standard value indicates a beneficial effect of the administered agent on the PAH condition in the subject.

Alternatively, a decrease in one or more CO estimates compared to the standard CO value, combined with one or more increased or stable PAP values compared to the standard PAP value can indicate no effect or a detrimental effect of the administered agent on the PAH condition in the subject. In another example, an increase in one or more PAP values compared to the standard PAP values, combined with a stable or decreased CO value compared to the standard CO value indicate no effect or a detrimental effect of the administered agent on the PAH condition in the subject.

The PAP values and or CO estimates can also be used to derive a third value indicative of progression or treatment of PAH. In this regard, as used herein, use of PAP and or CO values and estimates includes use or other values derived from PAP and CO. Derived metrics include Stroke Work and TPR, alone or in combination, which are within the definition of the use of CO and or PAP.

The administration of the pharmaceutical agent, for example, the agent administered, dosage, timing, protocol, or the like, can be modified or maintained after determining the effect of the agent of the PAH condition in the subject. For example, administration of the pharmaceutical agent is optionally maintained at its current dosage and or dosing regimen when improvement is indicated. In another example, the pharmaceutical agent is changed, or the dosage or dosing regimen modified when improvement is not indicated. In another example, the information obtained on PAP, CO, or both are used to determine an effective dosage or administration protocol for the agent or to evaluate the same, for example, in a clinical trial setting.

Therapeutic goals optionally include lowering or maintaining PAP and/or increase or maintain CO. Additional therapeutic goals include reducing or maintaining PVR. Optionally CO is increased while PAP is reduced in the subject. Optionally, CO or PAP is increased while PAP or CO is maintained respectfully. TPR is used as a surrogate for PVR in the context of PAH. If the etiology of disease is understood by RHC to be PAH with minimal component of left heart disease, change TPR can then be used to infer changes in PVR.

In the described methods, the obtained pulmonary artery pressure waveform is optionally obtained with a wireless sensor implanted in the subject. In addition, one or more of the standard pulmonary artery pressure values are optionally determined from a pulmonary artery pressure waveform obtained with a wireless sensor implanted in the subject. Therefore, the pulmonary artery pressure waveform is optionally obtained wirelessly and the standard values can be determined from a pulmonary artery waveform obtained wirelessly. In either case, the pulmonary artery pressure waveform is optionally obtained using an implanted sensor. Optionally, the implanted sensor is a pressure sensor, which is optionally implanted in the pulmonary artery of the subject. Optionally, the sensor lacks percutaneous connections. Optionally, the sensor is energized from an external source. Optionally, the sensor is a passive sensor energized to return pressure readings by an electromagnetic field.

Because of the nature of the sensors described above, the pulmonary artery pressure waveform is optionally obtained outside of a typical clinical evaluation environment. For example, the pulmonary artery waveform is optionally obtained while the subject is exercising. Exercising includes any activity of the subject. For example, exercise or exercising includes activities of daily living, prescribed exercise, walking, biking, running or the like. Optionally, the pulmonary artery pressure waveform is obtained while the subject is asleep.

An effective system and sensor for measurement of cardiovascular physiology information, such as obtaining the pulmonary artery pressure waveform is the CARDIOMEMS (Atlanta, GA) heart sensor. As described by U.S. Pat. No. 7,699,059 entitled "Implantable Wireless Sensor" and U.S. Pat. No. 7,679,355 entitled "Communicating with an Implanted Wireless Sensor," these sensors are MEMS-based sensors that are implanted in the pulmonary artery, more particularly in the distal pulmonary artery branch and are configured to be energized with RF energy to return high-frequency, high-fidelity dynamic pressure information from a precisely-selected location within a patient's body.

The sensors are optionally used to generate a real-time or substantially real-time pressure waveform. Via signal acquisition and processing techniques, a pressure waveform is optionally generated via a processor coupled with memory that contains the appropriate algorithm to relate the electrical characteristics of the circuit to the pressure of the PA.

In parallel or via discrete processors and memory elements, subsequent processing of the pressure waveform is performed. Summary values for each reading optionally include systolic PAP, diastolic PAP, mean PAP, heart rate, and estimated cardiac output.

PAP values are optionally determined by analysis of the pressure waveform to determine the average maximum waveform values for systolic PAP, average minimum waveform values for diastolic PAP, and average of all waveform values for mean PAP.

Heart Rate is optionally determined in the following manner: The timing of repetitive relevant hemodynamic events within the cardiac cycle, such as optionally the average time interval between consecutive systolic or diastolic pressure values, is used to determine the average time interval between beats. The average time interval between beats is optionally used to determine the average heart rate as 60 (s/min.)/average time interval between beats (s/beat) to determine the average heart rate in beats per minute.

Cardiac Output (CO) is estimated based on the pulmonary arterial pressure waveform using the following approach. For each cardiac cycle, the pulmonary arterial pressure waveform P(t), comprised of an array of consecutive discrete paired pressure (p) and time (t) values, P(t)={(p$_1$,t$_1$), (p$_2$,t$_2$) . . . }, is optionally analyzed to identify the following relevant reference pressure and time points for each beat:

P1,T1 pressure and time at start of systole and end of diastole.

P2,T2 pressure and time at end of the RV incident wave/beginning of reflected wave indicated as first upslope pressure incisura after the systolic upslope dP/dT max or alternatively at the maximum of the pressure beat.

P3,T3 pressure and time at end of systole/end of outflow demarcated by the dicrotic notch/pulmonic valve closure.

Optionally the pressure waveform features associated with the RV incident pressure wave, and time parameters during systole are used to determine a proportional estimation of stroke volume.

The proportional estimate of stroke volume for each beat, can be determined in a variety of ways, including but not limited to the following:

a. P2–P1
b. $\sqrt{P2}$
c. $\sqrt{(P2-P1)}$
d. $\sqrt{(average(P2, P3))}$
e. $\sqrt{P2} \times (T3-T1)$
f. $\sqrt{(P2-P1)} \times (T3-T1)$
g. $\sqrt{(average(P2,P3))} \times (T3-T1)$
h. $\sqrt{P2} \times (T3-T2)$
i. $\sqrt{(P2-P1)} \times (T3-T2)$
j. $\sqrt{(average(P2,P3))} \times (T3-T2)$
k. dP/dT max value between T1 and T2
l. Integration of P(t)–P1, from T1 to T2.
m. Integration of the first derivative of the pressure waveform, dP(t)/dT, from T1 to T2.
n. Integration of $\sqrt{(P(t)-P1)}$, from T1 to T2.
o. Integration of $\sqrt{dP(t)/dT}$, from T1 to T2.

Alternatively, for estimates which integrate pressure changes over time and which have a downstream reference pressure (P1) (l and n) may be replaced in the equation with a value that gradually increases as the pulmonary vasculature volume increases during filling along the line that is defined by endpoints P1,T1 and P3,T3, according to the equation;

$$P(t)_{[P1,T1 \text{ to } P3,T3]} = P1 + [(P3-P1)/(T3-T1)] \times (t-T1)$$

Accordingly, the proportional estimate of stroke volume can also be performed as follows:

p. Integration of P(t)–P(t)$_{[P1,T1 \text{ to } P3,T3]}$ from T1 to T2.
q. Integration of $\sqrt{(P(t)-P(t)_{[P1,T1 \text{ to } P3,T3]})}$, from T1 to T2.

Alternatively, for estimates that integrate pressure changes or the square root of pressure changes over time (l, n, p, and q), integration over the timeframe from T2 to T3 may also be included, with exclusion of the portion of the waveform which is attributed to the reflected wave. The reflected portion of the waveform is delineated by the line defined by endpoints P2,T2 and P3,T3, defined by the equation;

$$P(t)_{[P2,T2 \text{ to } P3,T3]} = P2 + [(P3-P2)/(T3-T2)] \times (t-T2)$$

Accordingly, the proportional estimate of stroke volume can also be performed as follows:

r. Integration of P(t)–P1, from T1 to T2 plus integration of P(t)$_{[P2,T2 \text{ to } P3,T3]}$–P1 from T2 to T3.
s. Integration of $\sqrt{(P(t)-P1)}$, from T1 to T2 plus integration of $\sqrt{(P(t)_{[P2,T2 \text{ to } P3,T3]}-P1)}$ from T2 to T3.
t. Integration of P(t)–P(t)$_{[P1,T1 \text{ to } P3,T3]}$ from T1 to T2 plus integration of P(t)$_{[P2,T2 \text{ to } P3,T3]}$–P(t)$_{[P1,T1 \text{ to } P3,T3]}$ from T2 to T3.
u. Integration of $\sqrt{(P(t)-P(t)_{[P1,T1 \text{ to } P3,T3]})}$, from T1 to T2 plus integration of $\sqrt{(P(t)_{[P2,T2 \text{ to } P3,T3]}-P(t)_{[P1,T1 \text{ to } P3,T3]})}$ from T2 to T3.

A proportional estimate of stroke volume ($SV_{prop.est}$). is determined as the average of the compiled proportional estimates from at least one cardiac cycle. The duration or number of cardiac cycles for the averaging window can be configured as appropriate to the application. The minimum average length preferably exceeds the length of at least one respiratory cycle in order to average variation attributable to the respiratory cycle.

A proportional estimate of cardiac output is determined by multiplying the average proportional estimate of stroke volume by the measured average heart rate.

An initial reference cardiac output measurement is performed for method calibration, typically during the sensor implantation procedure using a clinically accepted measurement method such as thermodilution, modified Fick, or Fick. During the same measurement session, one or more wireless pulmonary arterial pressure waveform readings are collected. An initial patient specific constant term ($A_0$) is calculated as the ratio of the reference cardiac output measurement and the proportional estimate of cardiac output determined during the same measurement session. This initial patient specific constant term indirectly determines the effects of other relevant parameters such as the RV outflow tract cross sectional area (CSA) and the initial characteristic impedance during the calibration measurements (($Z_{o,i}$); $A_0 = CSA \times Z_0$. This initial patient specific constant term is used as a calibration factor that is multiplied by the proportional estimate of cardiac output to produce the initial estimated cardiac output value; $CO_{est\_Zo,i} = A_o \times SV_{prop.est} \times HR$.

As a corollary to Ohm's law for electrical circuits, the relationship between pressure changes ($\Delta P$) and flow (Q) is governed by flow impedance (Z); $\Delta P(t) = Z(t) \times Q(t)$. Thus, the pressure based proportional estimate of stroke volume and cardiac output is valid only without relevant changes in impedance. This assumption is valid during short term assessments, as would be the case during an initial calibration reading of, for example, 18 s length. However, flow impedance may change over longer timeframes between readings. For this reason, also accounting for changes in impedance between readings is expected to yield improved model performance.

Flow impedance has frequency and non-frequency dependent components.

The frequency dependent components of impedance are primarily associated with reflected, propagated pressure waves which dynamically influence the relationship between pressure and flow. These frequency dependent effects are incorporated into the model through the previously presented use of the first upslope incisura as the T2 timepoint in the initial stroke volume estimate. For example, more prominent reflected pressure waves or faster pressure wave propagation associated with increased pulmonary vascular impedance results in an earlier first upslope incisura, which reduces the proportional estimate of stroke volume. Conversely, less prominent reflected pressure waves or slower pressure wave propagation associated with reduced pulmonary vascular impedance results in a later first upslope incisura, which results in an increased proportional estimate of stroke volume.

In one example, changes in the non-frequency dependent, characteristic impedance after initial calibration are incorporated into the model in order to achieve improved accuracy in the stroke volume and cardiac output estimates without need for recalibration over extended timeframes.

The physiological basis for the non-frequency dependent impedance change estimate, hereafter described as characteristic impedance change, $\Delta Z(t)$, is presented as follows. The input stroke volume is a bolus injection that is introduced into the pulmonary vasculature during a minor portion of the total cardiac cycle, indicated by the timeframe from start of systole to the first upslope incisura (T2–T1). Conversely, the outgoing stroke volume leaves the pulmonary vascular through the pulmonary capillaries throughout the entire cardiac cycle. During the relatively short input stroke volume timeframe, a minor portion of the pulmonary vascular blood volume leaves the pulmonary arterial vasculature through the pulmonary capillary beds, approximately (T2–T1)/(Time interval between beats), approximately <10% of the total outgoing stroke volume. Accordingly, changes in resistance have only a minor impact on the characteristic impedance during the short T2–T1 timeframe, and the pulmonary vasculature during the T2–T1 timeframe can be fairly approximated as a closed system, with the major component of characteristic impedance determined by the pulmonary vascular compliance, $\Delta V/\Delta P$.

With increased mean, systolic, or diastolic average pulmonary arterial pressures, the pulmonary arterial wall strain modulus increases, and compliance decreases in a predictable manner, due to the mechanical properties of the pulmonary vessels. (Pasierski T J, CHEST 1993). Based on this relationship, changes in mean, systolic, or diastolic average pulmonary pressures from baseline to a follow-up measurement can be used to infer proportional changes in characteristic impedance from baseline values.

The relationship between average pulmonary arterial pressure changes and proportional impedance changes was determined heuristically using data obtained from 54 NYHA Class III Heart Failure patients with 116 follow-up sets of reference cardiac output measurements and wireless pulmonary arterial pressure measurements performed a mean±st. dev. (min., max) of 463±422 (48, 1281) days post implant. The estimated Cardiac Output for follow-up measurements was determined using the initially determined constant term from baseline ($A_i$), which does not account for changing impedance: $CO_{est\text{-}Zo,i} = A_o \times SV_{prop.est} \times HR$. The effect of changing impedance was inferred using a scatter plot of the proportional residual error at follow-up, defined as $(CO_{est\_Zo,i} - CO_{ref})/CO_{est\_Zo,i}$, vs. changes in average pulmonary arterial pressure from baseline. There was an observed trend of residual error with respect to mean pressure changes for mean pressure changes in the provided example. The pattern of residual error as a function of mean pulmonary arterial pressure change over the threshold value from baseline to follow-up, $\Delta$mPAP, was characterized using an exponential regression, with constant term coefficient, B=−0.025, by the following equation (FIG. 5):

$$\text{Curve fit for proportional residual error at follow-up} = (CO_{est\_Zo} - CO_{ref})/CO_{est\_Zo} = 1 - e^{(B \times \Delta mPAP)} = 1 - e^{(-0.0255 \times \Delta mPAP)}$$

$$\text{Predicted residual error} = CO_{est\_Zo} - CO_{ref} = CO_{est\_Zo} \times (1 - e^{(-0.025 \times \Delta mPAP)})$$

In order to incorporate the impedance change effect, the predicted residual error is subtracted from $CO_{est\text{-}Zo,i}$ to produce a CO estimate with impedance change effects incorporated, $CO_{est\_Z}(t)$.

$$CO_{est\_Z(t)} = CO_{est\_Zo,i} - CO_{est\_Zo,i} \times (1 - e^{(-0.025 \times \Delta mPAP)}) = CO_{est\_Zo,i} \times e^{(-0.025 \times \Delta mPAP)}$$

Finally, it should be noted that model coefficients, such as but not limited to the mean pressure threshold value and exponential curve fit coefficient (B), can be used to optimize results based on best fit for a given population or individual patient, using sets of pressure waveform data and CO reference values measured at more than one time with relevant CO change between measurements.

Figure 6A:
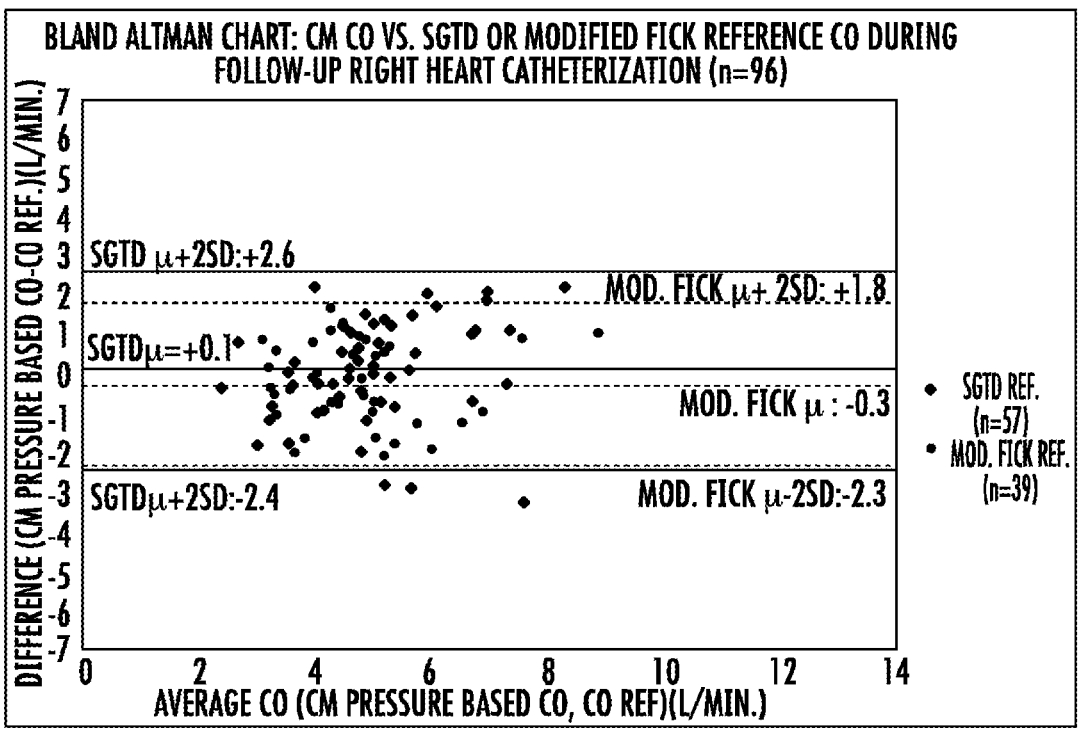
FIGS. 6A and 6B are graphs showing CO measurement Bland-Altman Agreement with an implantable CardioMEMS® (Atlanta, GA) sensor versus a CO reference standard.
Figure 6B:
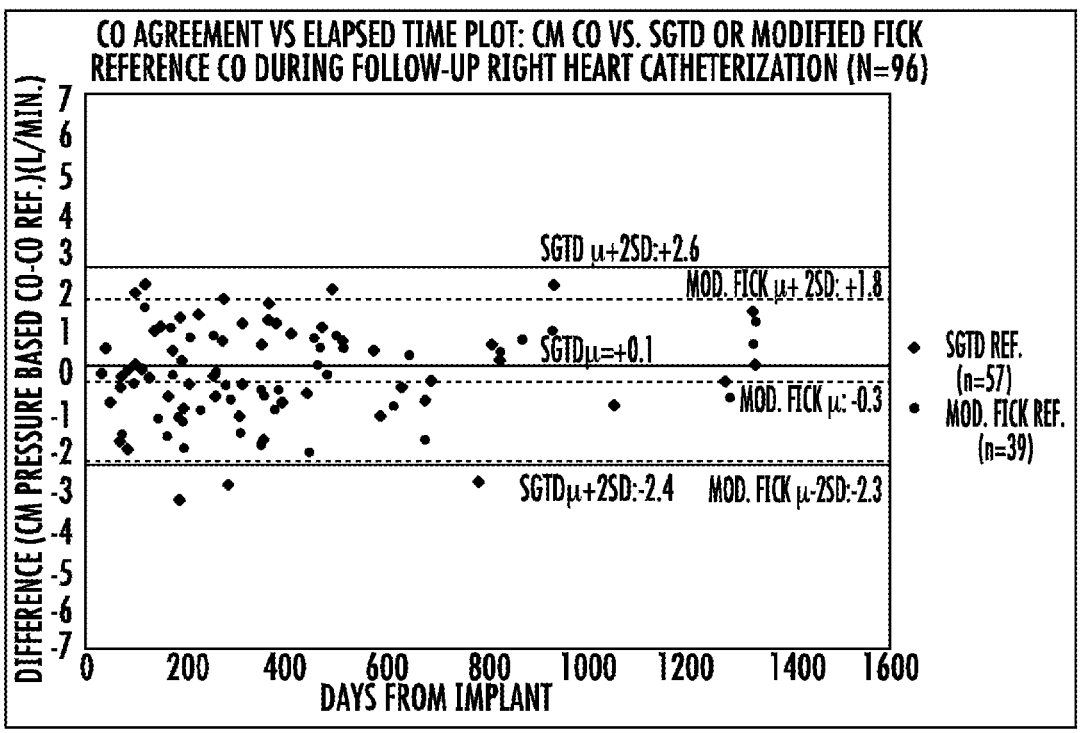

FIGS. 6A and 6B show Bland-Altman charts of CO estimate agreement with reference CO measurements performance using pressure data obtained from a CardioMEMS® (Atlanta, GA) wireless implantable sensor. FIG. 6A shows consistent accuracy agreement across the measurement range. FIG. 6B shows consistent accuracy agreement over extended timeframes.

As described above, provided herein are methods of predicting an outcome, evaluating progress or improvement, or treating PAH in a subject. Such methods include administering an effective amount of a pharmaceutical agent to the subject. Optionally, the pharmaceutical agents are contained within a pharmaceutical composition.

Provided herein are compositions containing the provided pharmaceutical agents and a pharmaceutically acceptable carrier described herein. The herein provided compositions are suitable of administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in Remington: The Science and Practice of Pharmacy, 21st Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the agent to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

According to the methods taught herein, the subject is administered an effective amount of the agent, or an effective amount, or dosage, or dosage regimen is determined. The terms effective amount and effective dosage are used interchangeably. The term effective amount is defined as any amount, for example, to produce a desired physiologic response.

Effective amounts and schedules for administering the agent may be determined using, for example, PAP and/or CO values and estimates as described herein. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. The dosage may vary with the age, condition, sex, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

In some examples, the effective dosage or amount, or an effective dosage or treatment regimen or protocol is that which lowers or maintains PAP and/or that raises or maintains CO at a desired level. For example, a desired PAP and/or CO level is a level that is expected to have an improved outcome compared to a previous PAP and/or CO level or levels in an individual or from a control determined from a population of individuals. Either may be referred to as a standard. Therefore, for example, an effective dose or amount is optionally that which reduces or maintains PAP and/or CO at a therapeutic level that is expected to result in an improved outcome or in one or more reduced or maintained clinical conditions.

As used herein, the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

Example 1: Evaluation of PAH Treatment Using an Implantable Pressure Sensor to Monitor PAP A 53 year old black male presented with PAH. As shown in FIG. 1, the subject initially presented with a PAP above 30 mm Hg. As further shown in FIG. 1, treatment with Lasix and then Metolaxone reduced PAP in the subject to below 25 mm Hg. The subject was maintained between about 25 mmHg and 10 mm Hg. The reduction and maintenance of PAP indicated successful treatment of PAH in the subject.

Figure 2A:
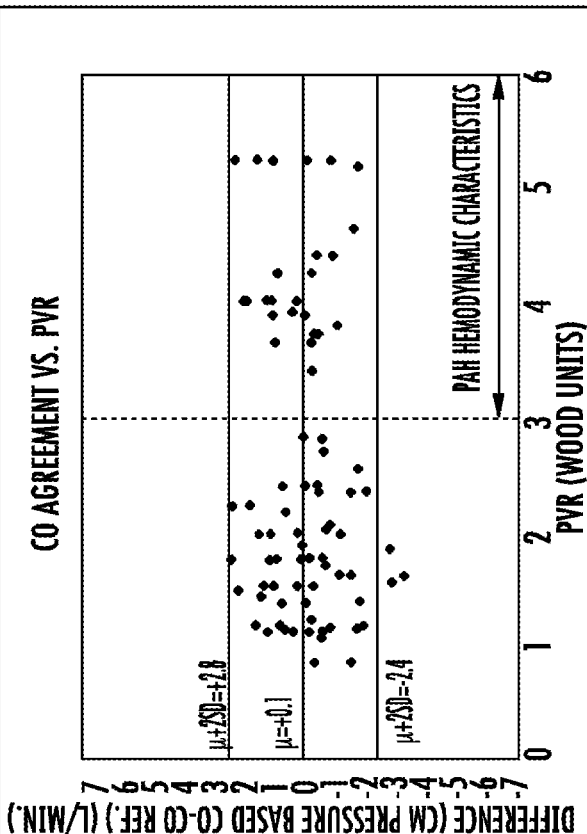
FIGS. 2A and 2B are graphs showing consistent and accurate CO measurements using an implantable sensor as described herein.
Figure 2B:
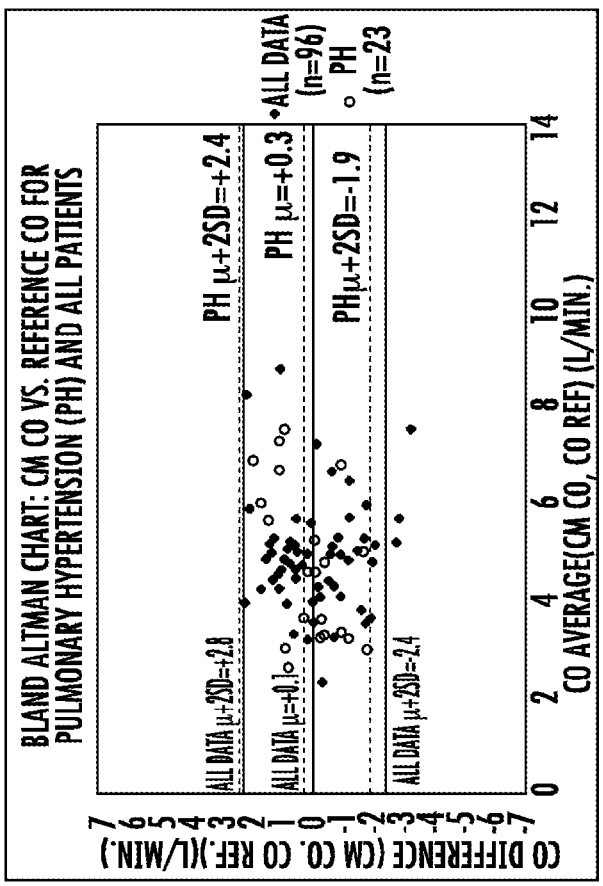

Example 2: Hemodynamic Parameters for Evaluation and Monitoring of PAH Using an Implantable Pressure Sensor As shown in FIGS. 2A and B, an implantable pressure sensor, as described herein, was used to evaluate CO. FIG. 2A indicates measurement of CO is subject having mPAP>25 and a PVR>3. As shown in FIG. 2B, CO was in agreement with PVR across a wide PVR range.

Figure 3:
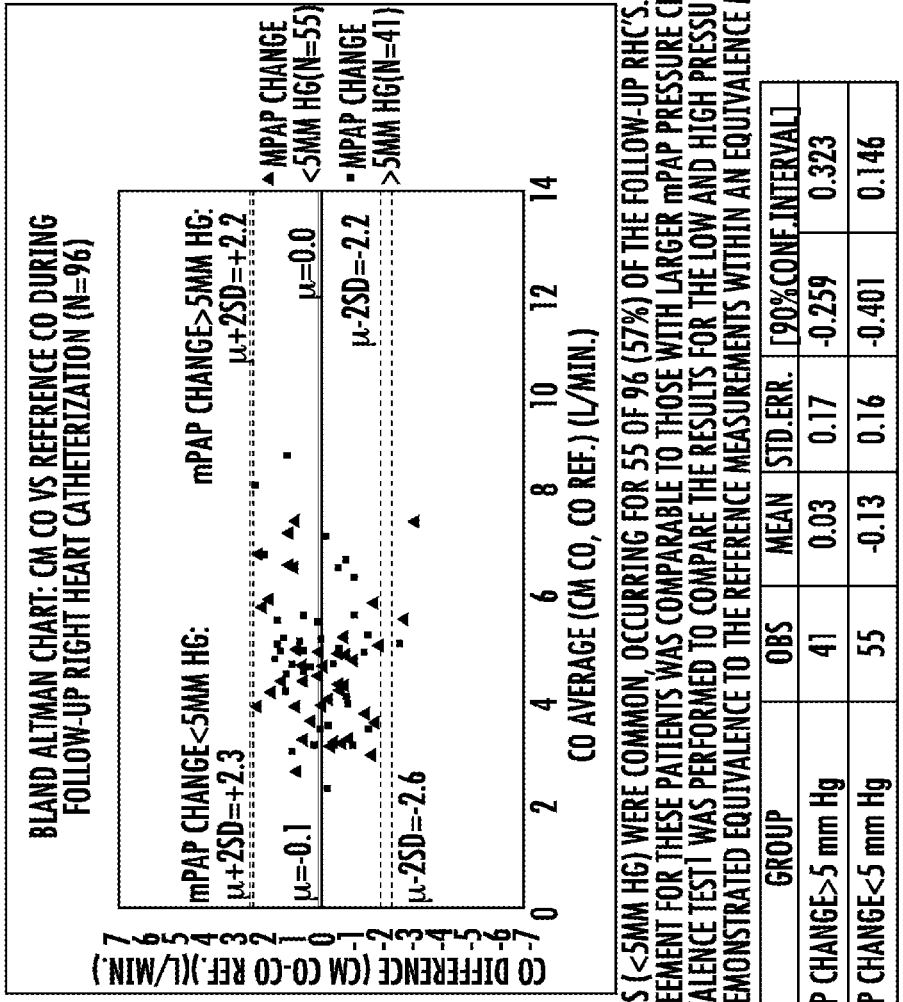
FIG. 3 is a graph showing CO agreement with pressure changes.

FIG. 3 shows CO agreement with small pressure changes. Small mPAP changes (<5 mm Hg) were common, occurring for 55 of 96 (57%) of right heart catheterization subjects. The level of CO agreement for these patients was comparable with larger mPAP changes. A one sample equivalence test was performed to compare the results for the low and high pressure change groups. This test demonstrated equivalence to the reference measurements with an equivalence margin of 0.5 L/min.

Figure 4:
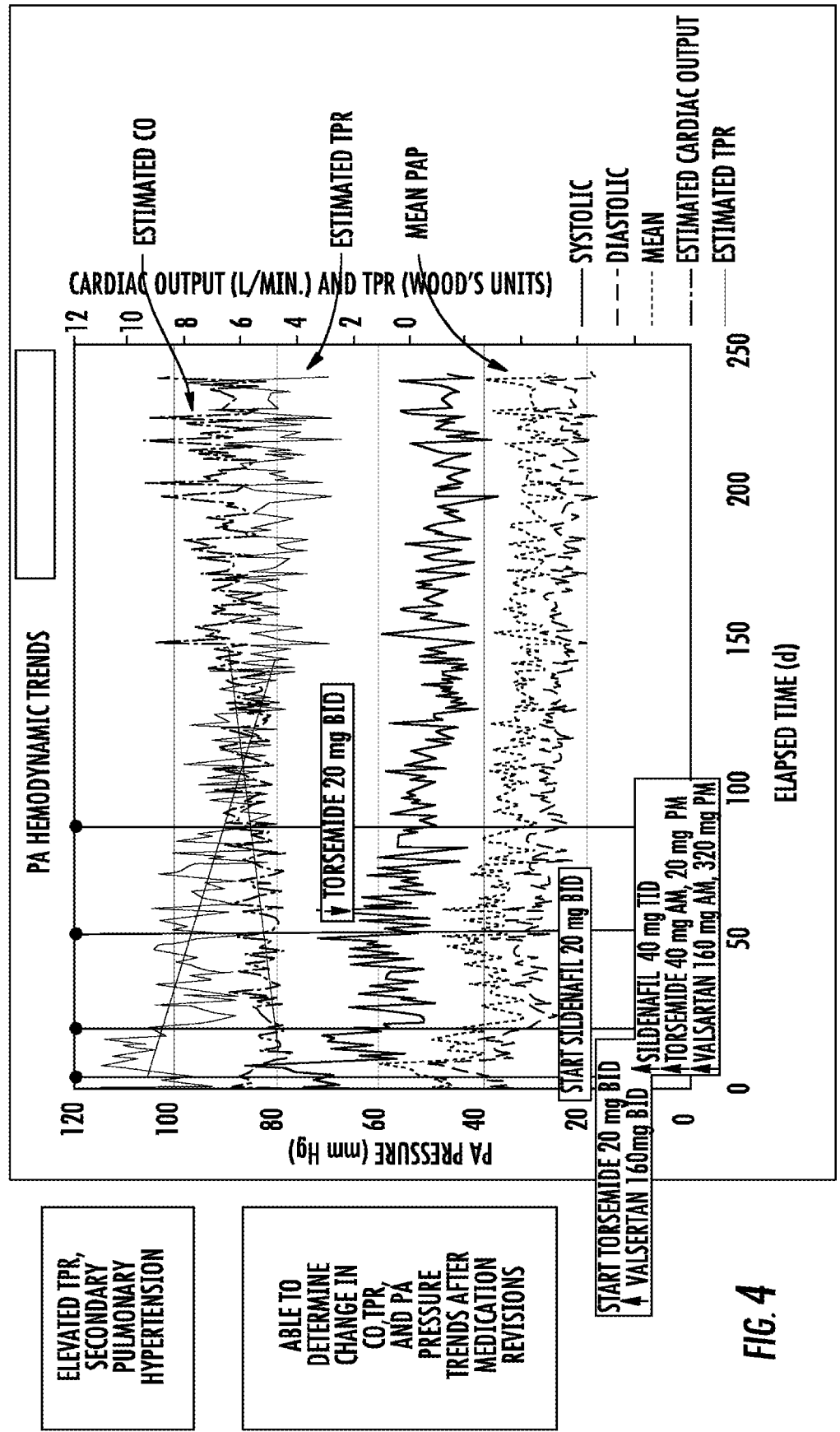
FIG. 4 is a graph showing trends in CO, mPAP and TPR in a PAH subject before and after administration of treatment agents.

FIG. 4 shows use of the implantable sensors described herein to determine changes in CO, TPR and PAP after medication revisions in subjects having PAH. As shown, the estimated CO was shown to rise after medication revision, while the TPR and mPAP were reduced. The data show the progression of PAH in subject following treatment. The data show trends in mPAP, CO and TPR in a subject with PAH. The data further show the combined use of mPAP, CO and TPR trends in monitoring a subject having PAH prior and subsequent to administration of a treatment to the subject.

Figure 5:
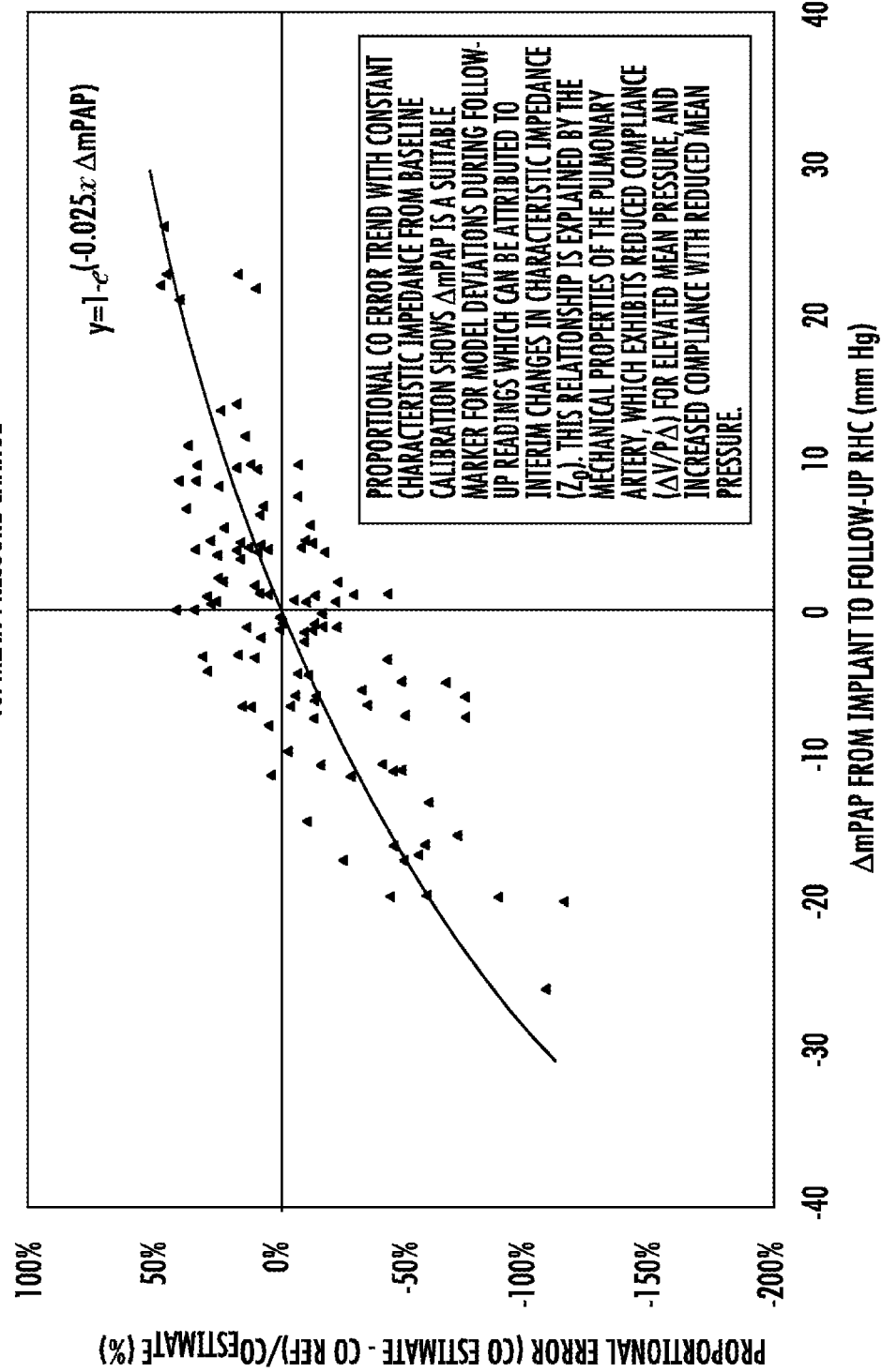
FIG. 5 is a graph showing estimated Cardiac Output.

FIG. 5 shows the estimated Cardiac Output during the follow-up measurement was determined using the initially determined constant term from baseline ($A_o$), which does not account for changing impedance: $CO_{est\text{-}Zo,i} = A_f \times SV_{prop.est} \times HR$. The effect of changing impedance was inferred by a scatter plot of the proportional residual error at follow-up, defined as $(CO_{est\_Zo,i}-CO_{ref})\;CO_{est\_Zo,i}$, relative to changes in average pulmonary arterial pressure from baseline. There was an observable trend of residual error with respect to mean pressure changes for mean pressure changes over a threshold value, over 25 mm Hg in the provided example. The pattern of residual error as a function of mean pulmonary arterial pressure change over the threshold value from baseline to follow-up, ΔmPAP, was characterized using an exponential regression, with constant term coefficient B=0.03.

FIG. 6 shows Bland-Altman charts of CO estimate agreement with reference CO measurements performance using pressure data obtained from a CardioMEMS® (Atlanta, GA) wireless implantable sensor. The left hand chart shows consistent accuracy agreement across the measurement range. The right hand chart shows consistent accuracy agreement over extended timeframes.

Figure 7:
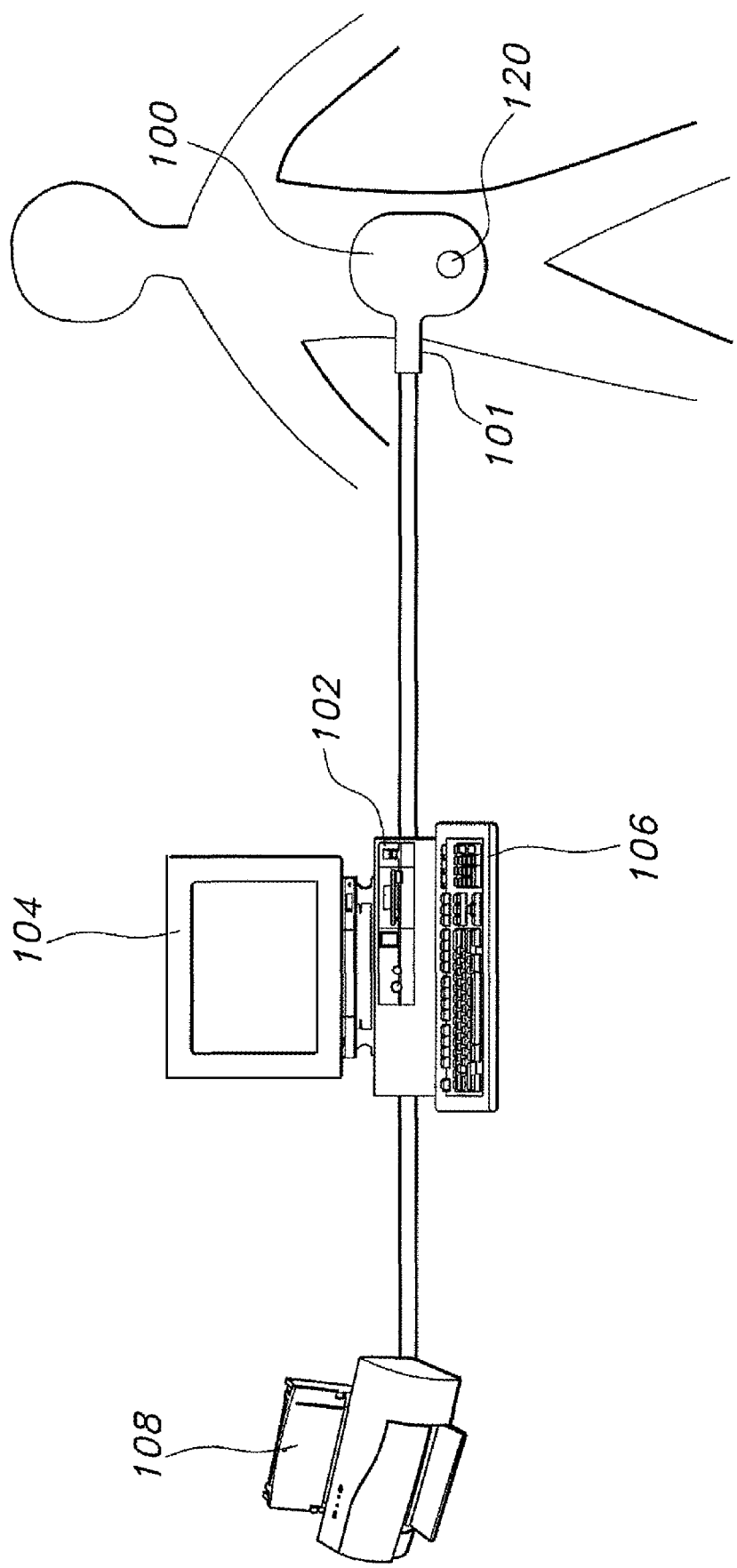
FIG. 7 illustrates an exemplary system for communicating with a wireless sensor implanted within a body.

FIG. 7 illustrates an exemplary system for communicating with a wireless sensor implanted within a body. The system includes a coupling loop 100, a base unit 102, a display device 104 and an input device 106, such as a keyboard.

The coupling loop is formed from a band of copper. In one embodiment, the loop is eight inches in diameter. The coupling loop includes switching and filtering circuitry that is enclosed within a shielded box 101. The loop charges the sensor and then couples signals from the sensor into the receiver. The antenna can be shielded to attenuate in-band noise and electromagnetic emissions.

Another possible embodiment for a coupling loop includes separate loops for energizing and for receiving, although a single loop can be used for both functions. PIN diode switching inside the loop assembly is used to provide isolation between the energizing phase and the receive phase by opening the RX path pin diodes during the energizing period, and opening the energizing path pin diodes during the coupling period. Multiple energizing loops can be staggered tuned to achieve a wider bandwidth of matching between the transmit coils and the transmit circuitry.

The base unit includes an RF amplifier, a receiver, and signal processing circuitry.

The display 104 and the input device 106 are used in connection with the user interface for the system. In the embodiment illustrated in FIG. 7 the display device and the input device are connected to the base unit. In this embodiment, the base unit also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software is used to provide the user interface, as well as to provide graphics, store and organize data and perform calculations for calibration and normalization. The user interface records and displays patient data and guides the user through surgical and follow-up procedures.

An optional printer 108 is connected to the base unit and can be used to print out patient data or other types of information. As will be apparent to those skilled in the art other configurations of the system, as well as additional or fewer components can be utilized with the invention.

Patient and system information can be stored within a removable data storage unit, such as a portable USB storage device, floppy disk, smart card, or any other similar device. The patient information can be transferred to the physician's personal computer for analysis, review, or storage. An optional network connection can be provided to automate storage or data transfer. Once the data is retrieved from the system, a custom or third party source can be employed to assist the physician with data analysis or storage.

FIG. 7 illustrates the system communicating with a sensor 120 implanted in a patient. The system is used in two environments: 1) the operating room during implant and 2) the doctor's office during follow-up examinations. During implant the system is used to record at least two measurements. The first measurement is taken during introduction of the sensor for calibration and the second measurement is taken after placement for functional verification of the stent graft. The measurements can be taken by placing the coupling loop either on or adjacent to the patient's back or the patient's stomach for a sensor that measures properties associated with an abdominal aneurysm. For other types of measurements, the coupling loop may be placed in other locations. For example, to measure properties associated with the heart, the coupling loop can be placed on the patient's back or the patient's chest.

The system communicates with the implanted sensor to determine the resonant frequency of the sensor. As described in more detail in the patent documents referenced in the Background section, a sensor typically includes an inductive-capacitive ("LC") resonant circuit having a variable capacitor. The distance between the plates of the variable capacitor varies as the surrounding pressure varies. Thus, the resonant frequency of the circuit can be used to determine the pressure.

The system energizes the sensor with an RF burst. The energizing signal is a low duty cycle, gated burst of RF energy of a predetermined frequency or set of frequencies and a predetermined amplitude. Typically, the duty cycle of the energizing signal ranges from 0.1% to 50%. In one embodiment, the system energizes the sensor with a 30-37.5 MHz fundamental signal at a pulse repetition rate of 100 kHz with a duty cycle of 20%. The energizing signal is coupled to the sensor via a magnetic loop. This signal induces a current in the sensor which has maximum amplitude at the resonant frequency of the sensor. During this time, the sensor charges exponentially to a steady-state amplitude that is proportional to the coupling efficiency, distance between the sensor and loop, and the RF power. The speed at which the sensor charges is directly related to the Q (quality factor) of the sensor. Therefore, the "on time" of the pulse repetition duty cycle is optimized for the Q of the sensor. The system receives the ring down response of the sensor via magnetic coupling and determines the resonant frequency of the sensor. When the main unit is coupling energy at or near the resonant frequency of the sensor, the amplitude of the sensor return is maximized, and the phase of the sensor return will be close to zero degrees with respect to the energizing phase. The sensor return signal is processed via phase-locked-loops to steer the frequency and phase of the next energizing pulse.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

What is claimed is:

1. A method of evaluating progress of pulmonary arterial hypertension (PAH) in a subject, or an outcome in the subject having PAH, comprising:
    obtaining pulmonary artery pressure (PAP) data over a cardiac cycle from a wireless pressure sensor implanted in a pulmonary artery of the subject, the wireless pressure sensor wirelessly communicating with a base unit, the base unit communicating with a second computer;
    utilizing a processor of at least one of the base unit or second computer for:
        determining first and second PAP values experienced within the pulmonary artery based on the PAP data;
        estimating first and second cardiac outputs (COs) based on the first and second PAP values experienced within the pulmonary artery over the cardiac cycle;
        comparing the first and second PAP values and comparing the first and second COs;
        monitoring a PAH progression or outcome in the subject based on the comparing of first and second PAPs and first and second COs; and
        changing at least one of a pharmaceutical agent, dosage or dosing regimen based on the PAH progression or outcome in the subject.

2. The method of claim 1, further comprising: communicating the PAP data from the wireless pressure sensor to the base unit, the processor of the base unit performing the determining, estimating, and comparing.

3. The method of claim 1, further comprising: transferring the first and second PAP values and the first and second COs from the base unit to the second computer.

4. The method of claim 3, further comprising: communicating the PAP data from the wireless pressure sensor to the base unit and to the second computer, the processor of the second computer performing the determining, estimating, and comparing.

5. The method of claim 1, further comprising transferring, from the base unit to the second computer, at least one of the i) first and second PAP values, ii) first and second COs, or iii) the PAP progression or outcome.

6. The method of claim 1, further comprising maintaining a network connection between the base unit and second computer.

7. The method of claim 1, wherein:
    a. a decrease in the first PAP value compared to the second PAP value combined with the first CO estimate having increased or remained stable in comparison to the second CO estimate, or
    b. the first PAP value being stable when compared to the second PAP value combined with the first CO estimate having increased when compared to the second CO estimate,
    indicates or predicts improvement of the PAH in the subject.

8. The method of claim 1, wherein the pressure sensor lacks percutaneous connections.

9. The method of claim 1, further comprising energizing the pressure sensor from the base unit.

10. The method of claim 1, further comprising maintaining administration of the pharmaceutical agent at its current dosage and/or dosing regimen when improvement is indicated.

11. A system of evaluating progress of pulmonary arterial hypertension (PAH) in a subject, or an outcome in the subject having PAH, comprising:
    a wireless pressure sensor configured to be implanted in a pulmonary artery of the subject obtain and to obtain pulmonary artery pressure (PAP) data over a cardiac cycle;
    a base unit configured to wirelessly communicate with the pressure sensor;
    a second computer configured to communicate with the base unit;
    at least one of the base unit or second computer including a processor configured to:
        determine first and second PAP values experienced within the pulmonary artery based on the PAP data;
        estimate first and second cardiac outputs (COs) based on the first and second PAP values experienced within the pulmonary artery over the cardiac cycle;
        compare the first and second PAP values and comparing the first and second COs;
        monitor a PAH progression or outcome in the subject based on the comparing of first and second PAPs and first and second COs; and
        change at least one of a pharmaceutical agent, dosage or dosing regimen based on the PAH progression or outcome in the subject.

12. The system of claim 11, wherein the base unit includes a first processor that is configured to receive the PAP data from the wireless pressure sensor, determine the first and second PAP values, estimate the first and second COs, the base unit including memory configured to store the first and second PAP values and the first and second COs.

13. The system of claim 11, further comprising a network connection configured to transfer the first and second PAP values and the first and second COs from the base unit to the second computer.

14. The system of claim 11, wherein the second computer includes a first processor that is configured to receive the PAP data, determine the first and second PAP values, estimate the first and second COs, the second computer including memory configured to store the first and second PAP values and the first and second COs.

15. The system of claim 11, wherein the base unit is configured to transfer, to the second computer, at least one of the i) first and second PAP values, ii) first and second COs, or iii) the PAP progression or outcome.

16. The system of claim 11, wherein the pressure sensor is a passive sensor energized to return pressure readings by an electromagnetic field.

17. The system of claim 11, wherein the wireless pressure sensor is configured to collect PAP data that defines a pulmonary artery pressure waveform while the subject is exercising.

18. The system of claim 11, wherein the wireless pressure sensor is configured to collect PAP data that defines a pulmonary artery pressure waveform while the subject is asleep.

19. The system of claim 11, wherein the processor is further configured automatically to modify or maintain the administration of the pharmaceutical agent.

20. The system of claim 11, wherein the processor is further configured to maintain administration of the pharmaceutical agent at its current dosage and/or dosing regimen when improvement is indicated.

* * * * *